US00PP21578P2

(12) United States Plant Patent
Burnett

(10) Patent No.: US PP21,578 P2
(45) Date of Patent: Dec. 21, 2010

(54) APPLE TREE NAMED 'BURNETT CULTIVAR'

(50) Latin Name: *Malus domestica*
Varietal Denomination: Burnett

(76) Inventor: Pat Burnett, 12002 Burnett Rd., Leavenworth, WA (US) 98826

( * ) Notice: Subject to any disclaimer, the term of this patent is extended or adjusted under 35 U.S.C. 154(b) by 0 days.

(21) Appl. No.: 12/455,580

(22) Filed: Jun. 2, 2009

(51) Int. Cl.
*A01H 5/00* (2006.01)

(52) U.S. Cl. ..... Plt./162

(58) Field of Classification Search ..... Plt./162
See application file for complete search history.

(56) References Cited

U.S. PATENT DOCUMENTS

PP3,637 P 10/1974 McKenzie
PP4,121 P 10/1977 Ten Hove
PP8,621 P 3/1994 Olsen

*Primary Examiner*—Annette H Para
(74) *Attorney, Agent, or Firm*—Christensen O'Connor Johnson Kindness PLLC

(57) ABSTRACT

A new and distinct variety of apple tree, *Malus domestica*, denominated Burnett Cultivar, which is similar to Obrogala Cultivar (also known as 'Ultrared Gala', U.S. Plant Pat. No. 8,621) but which has an earlier harvest maturity date, less sugar at harvest, and less starch at harvest than 'Ultrared Gala'.

7 Drawing Sheets

Latin name of the genus and species claimed: *Malus domestica.*

Variety denomination: 'Burnett'.

BACKGROUND OF THE INVENTION

The distinct and new variety was discovered as a limb mutation by Pat Burnett in August 1999 in a block of Obrogala cultivar apples (U.S. Plant Pat. No. 8,621, hereinafter referred to as 'Ultrared Gala') at a ranch in Quincy, Wash. 'Ultrared Gala' is a mutation of the Tenroy cultivar (U.S. Plant Pat. No. 4,121) and the Tenroy cultivar is a mutation of the Kidd's D-8 cultivar (U.S. Plant Pat. No. 3,637). Apples of the "mother" tree limb were noted to be nearly fully colored and mostly a red blush in a appearance with a light stripe that is of a darker red and matures two weeks earlier than other standard maturing 'Galas.' The mother tree was planted in 1995, and is on M9 rootstock. Second generation trees were asexually reproduced by grafting on NIC 29 rootstock, planted in 2004, at the ranch in Quincy, Wash. Fruit from the second generation trees were observed in 2006, and again in 2007, and found to be identical to that of the mother branch mutation in appearance, maturity date, and maturity indices.

BRIEF SUMMARY OF THE INVENTION

The new variety shows all the typical morphological traits of that exhibited by its parent 'Ultrared Gala' and that of other 'Gala' strains. The tree structure, bark, bloom and bloom dates, fruit shape, and internal morphology, flavor and eating quality is the same as that exhibited by other 'Gala' strains grown in the Central Washington State region except as noted herein. Skin color and skin appearance is similar to that of 'Ultrared Gala.' The new variety exhibits one major and very significant difference to all other strains of 'Gala' grown in Central Washington State, namely, its early maturity date in relationship to its parent variety and the other strains of 'Gala'. The new variety has a harvest maturity date that is two weeks in advance of that exhibited by 'Ultrared Gala.' Other commercial strains of Gala apple grown in Central Washington exhibit harvest dates at or very near that exhibited by 'Ultrared Gala.' The new variety has been compared to 'Ultrared Gala' and found to exhibit higher pressures at harvest (24.7 pounds as to compared to 19.5 pounds for 'Ultrared Gala'), less sugar than 'Ultrared Gala' at harvest (11.6 brix as compared to 14.1 brix for 'Ultrared Gala') and slightly less starch at harvest maturity than 'Ultrared Gala' (1.8 as compared to 2.1 for 'Ultrared Gala').

BRIEF DESCRIPTION OF THE DRAWINGS

The accompanying photographs show the following characteristics of this new variety:

FIG. 7 is a chart comparing characteristics of the new variety ('Burnett') with two samples of 'Ultrared Gala', one sample of 'Ultrared' and one sample of 'Burnett' having been harvested on Aug. 13, 2007; and another sample of 'Ultrared' having been harvested on Aug. 27, 2007.

DETAILED BOTANICAL DESCRIPTION

Figure 1:
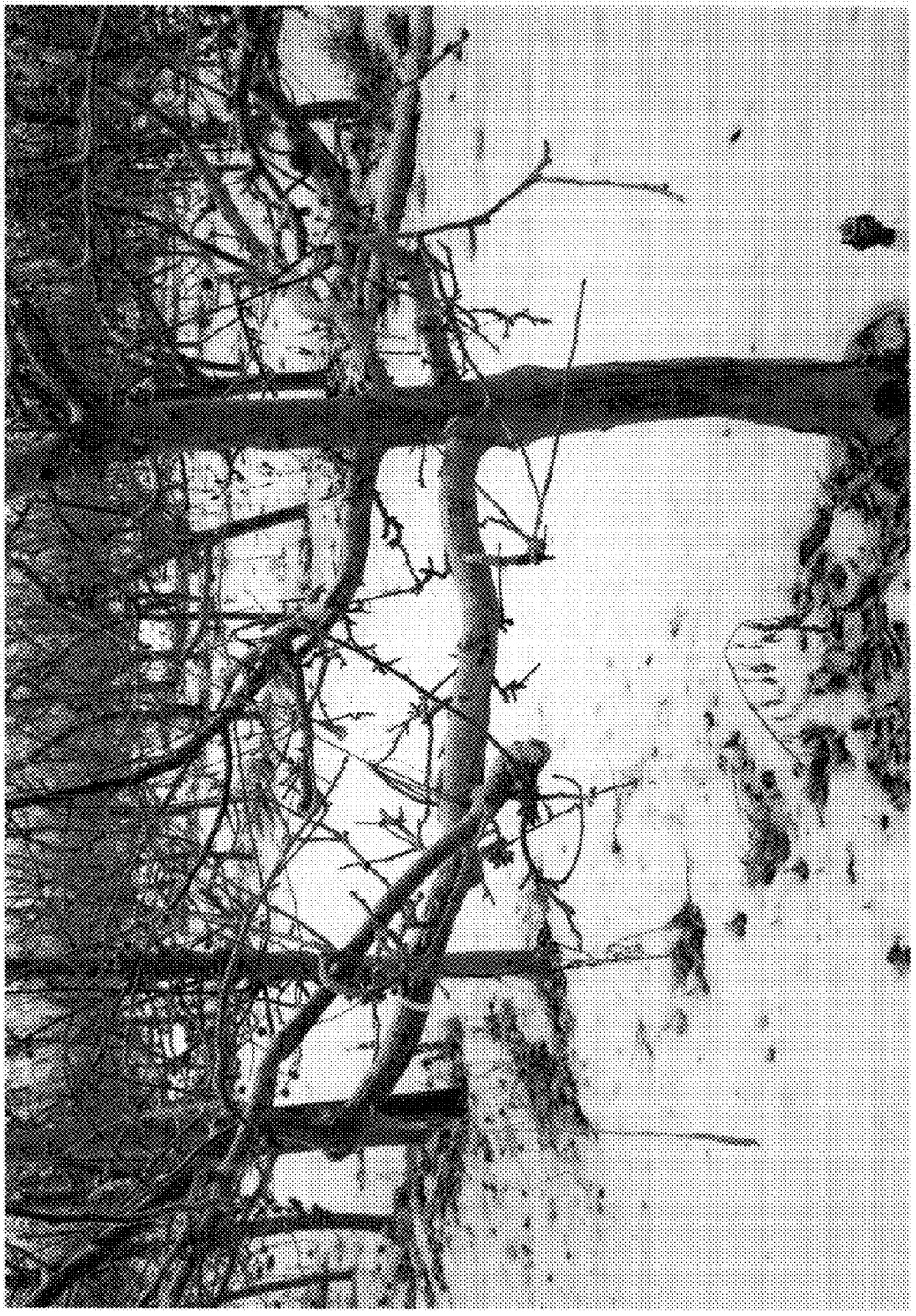
FIG. 1 is a photograph of the 'Ultrared Gala' apple mother branch (flagged blue) on 12-year-old 'Ultrared Gala' at winter dormancy.
Figure 2:
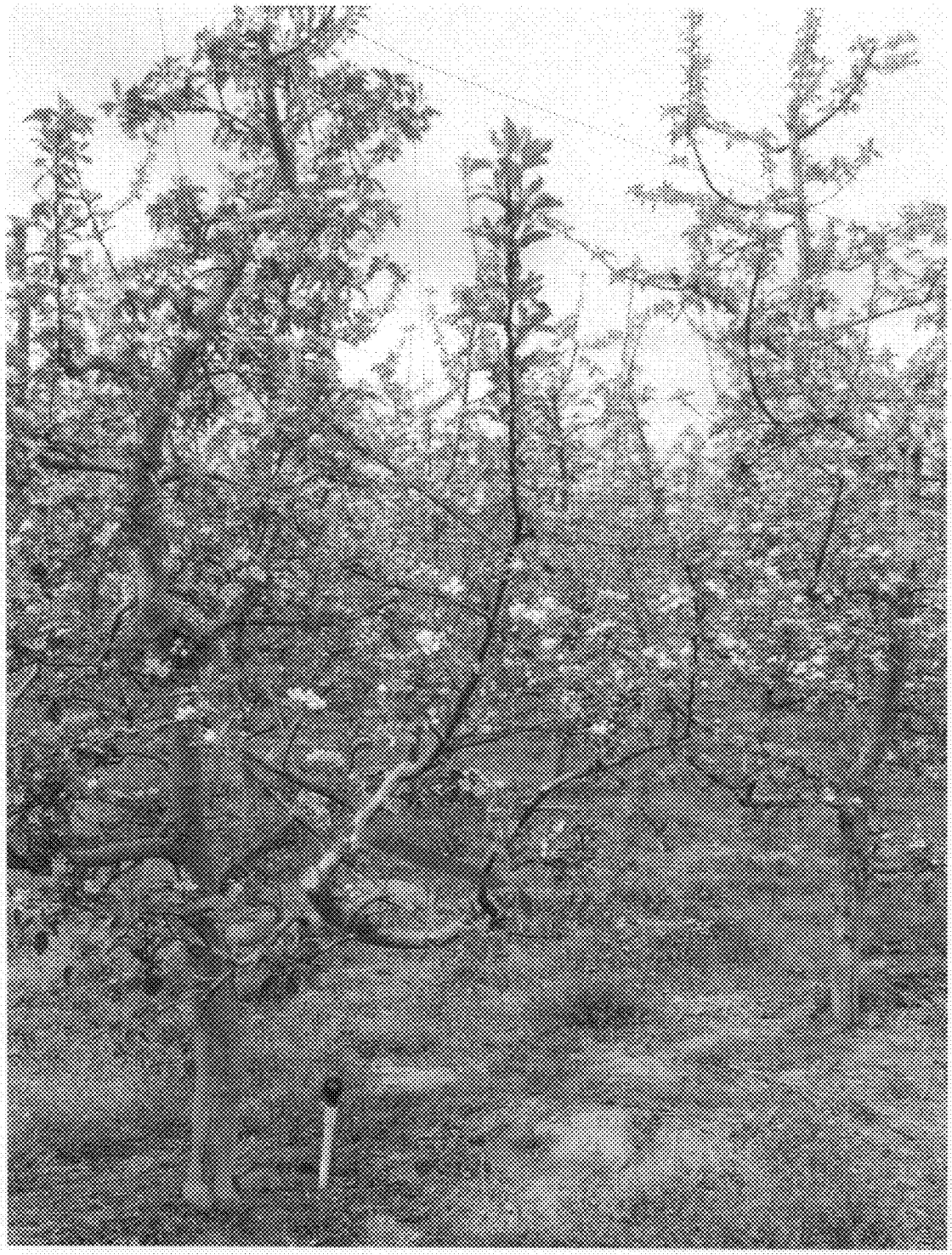
FIG. 2 is a photograph of the mother tree with the mother branch (flagged blue) at full bloom.
Figure 3:
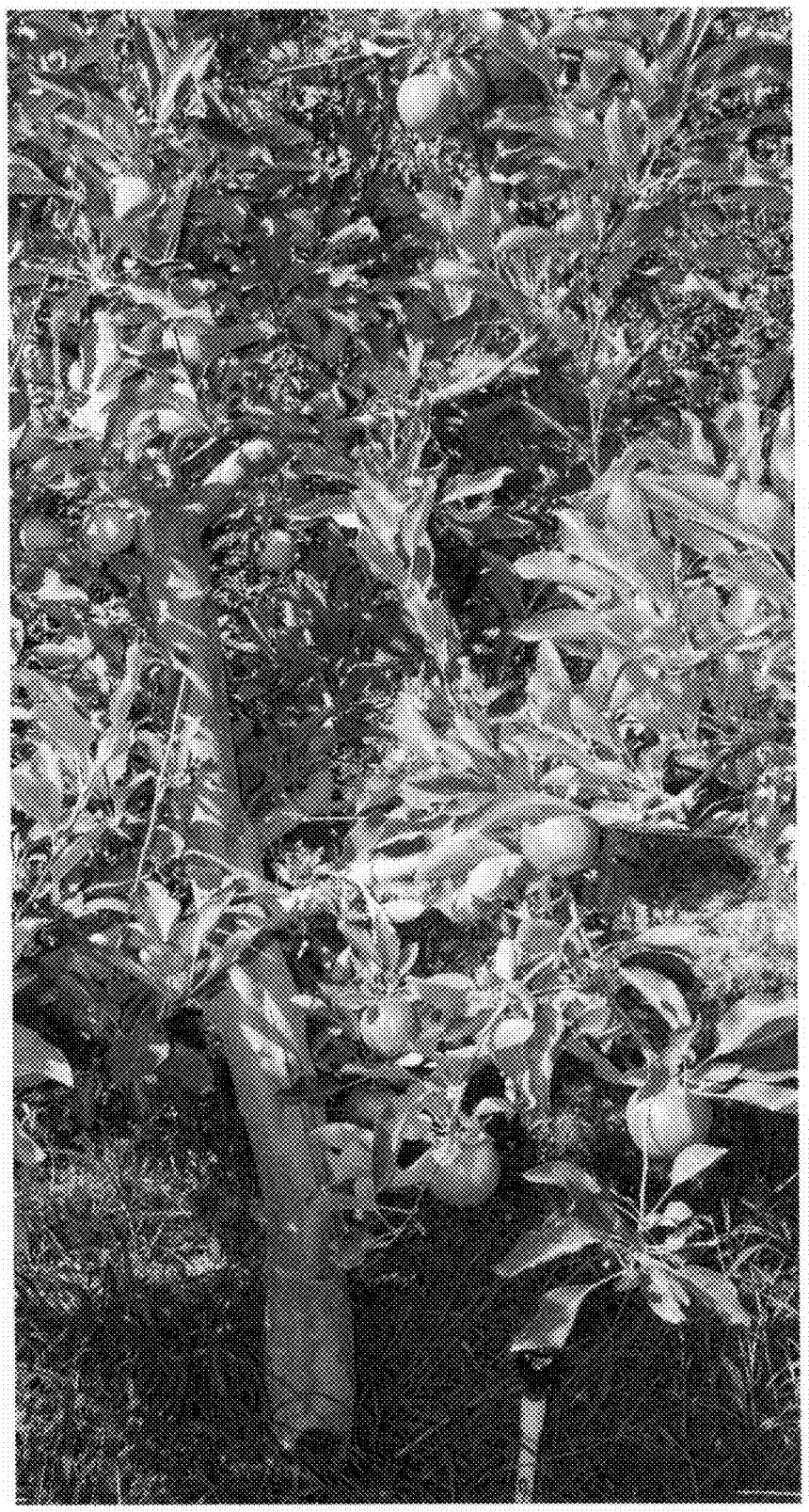
FIG. 3 is a photograph of fruiting limbs of the mother tree at harvest maturity.
Figure 4:
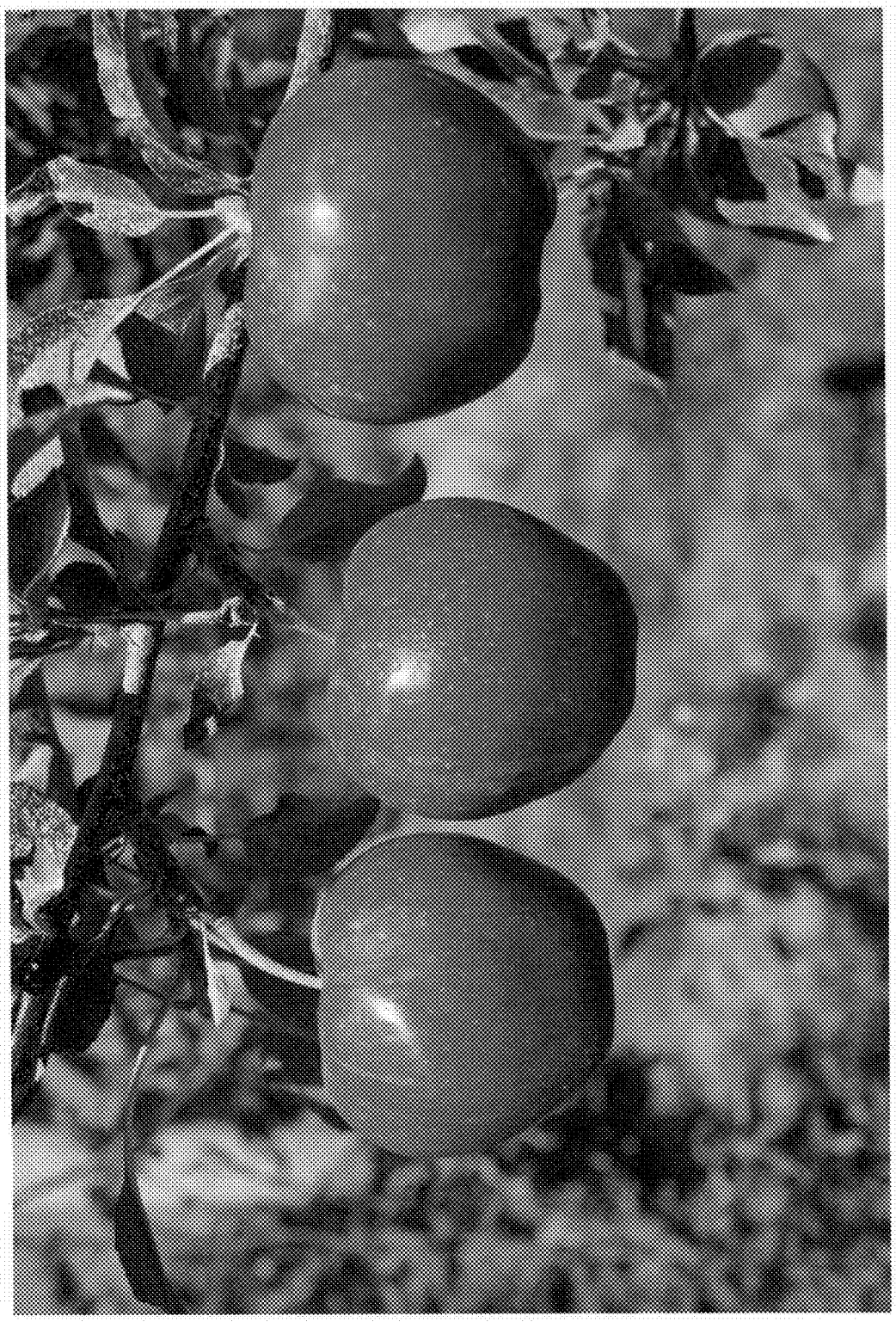
FIG. 4 is a close-up photograph of a fruiting limb of second generation apples of the new variety at harvest maturity, Aug. 13, 2007.
Figure 5:
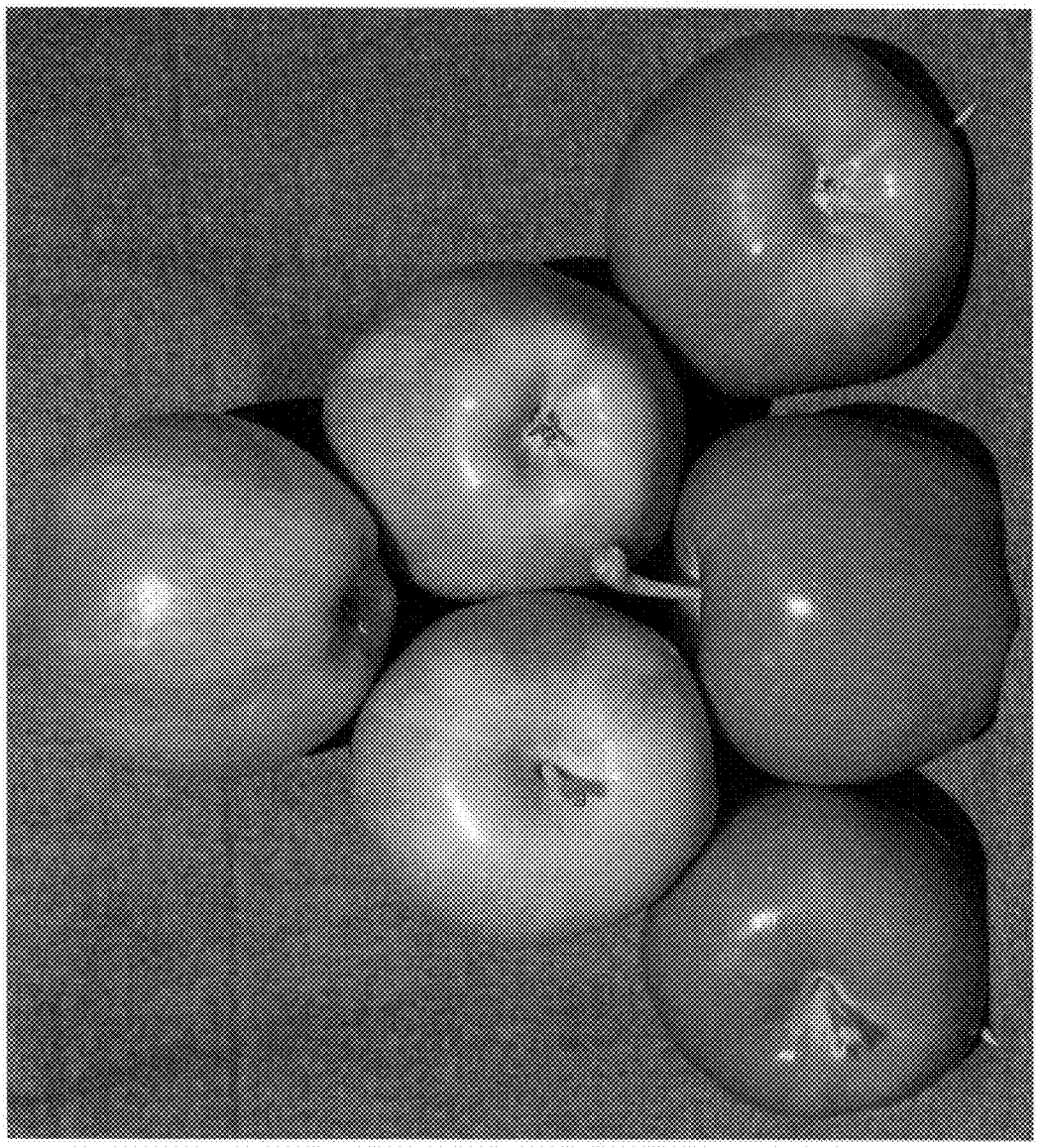
FIG. 5 is a comparison photograph of apples of the new variety (bottom three apples of the pyramid) and 'Ultrared Gala' (top three apples) harvested on Aug. 13, 2007.
Figure 6:
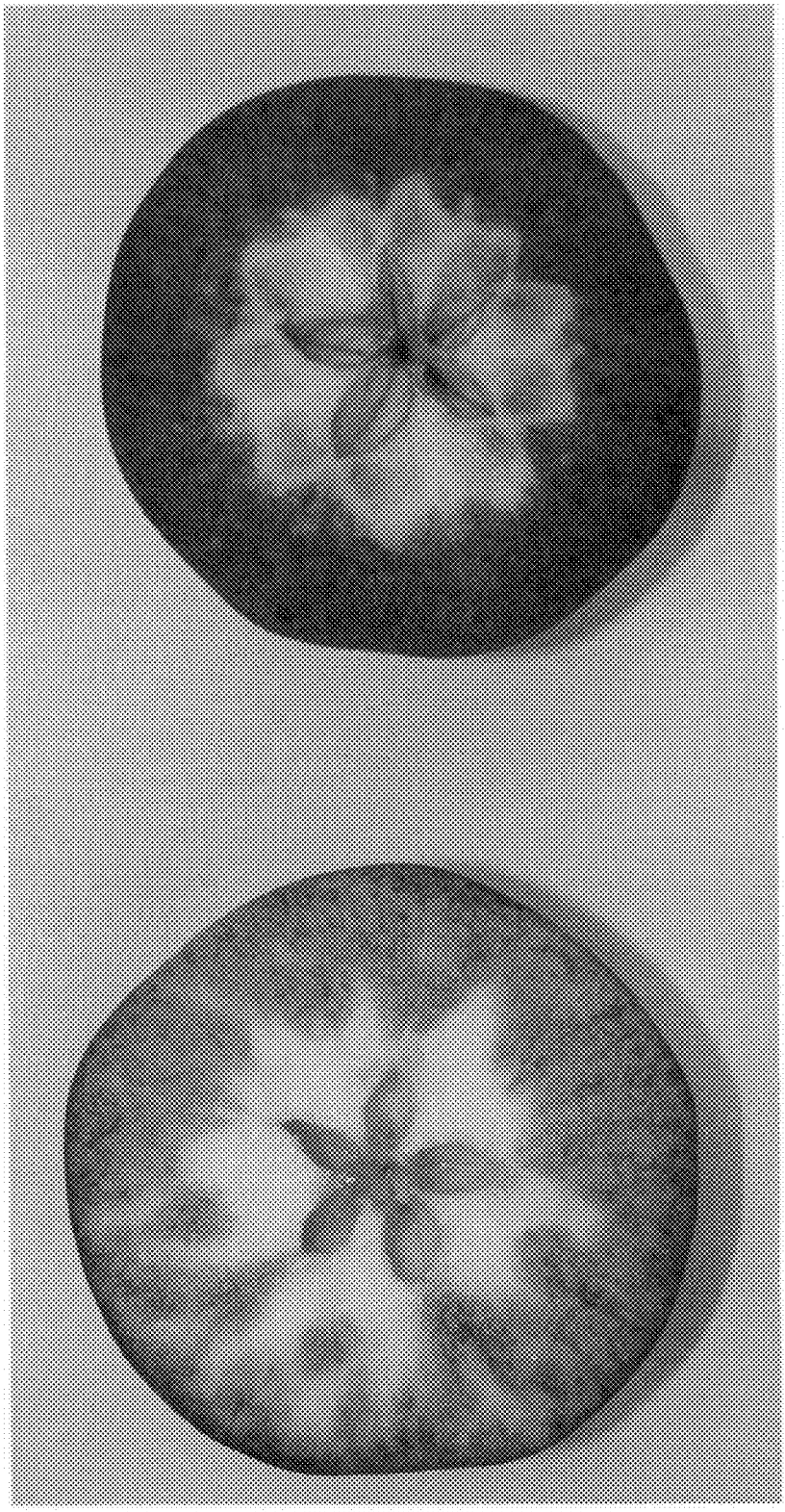
FIG. 6 is a photograph showing stained cross-sections for comparing the internal starch content between the new variety (right) and 'Ultrared Gala' (left), the samples having been harvested on Aug. 13, 2007.

The following detailed description of the characteristics of the new variety of apple tree is based on observations of three-year-old, second generation trees during the 2006 and 2007 seasons. Color terminology is in accordance with The Royal Horticulture Society Colour chart (see www.rhs.org.uk/Learing/Publication/pubs_library_color-chart.htm).

Tree:

*Size.*—Medium size typical of other 'Gala' trees (mother tree is 19 feet high by 10 feet wide; three-year-old, second generation trees average 9 feet high by 6 feet wide).

*Vigor.*—Moderately vigorous, similar to that of the adjacent 'Ultrared Gala' trees.

*Overall shape.*—Spreading and open.

*Hardiness.*—Hardy in area where discovered and tested; same as for 'Ultrared Gala'.

*Productivity.*—Productive; same as for 'Ultrared Gala'.

*Trunk size.*—The mother tree has a diameter of 4.5 inches at 18 inches above the soil line; the three-year-old, second generation trees average 1.6 inches in diameter at 18 inches above the soil line.

*Trunk bark texture.*—Smooth.

*Trunk bark color.*—From the grey group 201B.

*Lenticels.*—Present and few to moderate in number on the mother tree (3.3 mm to 11.9 mm long, with an average of 7.3 mm; 1.8 mm to 4.1 mm wide, with an average of 2.6 mm); present and moderate in number on the three-year-old, second generation trees (2.0 to 6.6 mm long, average of 3.7 mm; 1 mm wide); lenticel color is from the greyed purple group N187D.

Branches:

*First-year branches.*—Considered numerous in number, with no spur development; exhibit a spreading habit with crotch angles of 45 to 90 degrees; diameter at mid-point of shoot averages 4.3 mm, with an average length of 35.2 cm.

*Color.*—From the greyed orange group 166A. Lenticels: are numerous, with approximately 30 per linear cm; small and oval in shape, ranging in length from 0.4 to 0.75 mm and 0.3 to 0.6 in width; color is from the white group 155A. Branch pubescence: present but light and covering the complete circumference of the shoot. Internode: Spacing ranges from 26 to 55 mm, with an average of 46.5 mm.

*Scaffold branches (from 2nd generation tree).*—Moderate in number; spreading habit with crotch angles of 45 to 80 degrees. Color: from the greyed orange group 177A. Lenticels: present, numerous, both round and elongated shapes present; 40% are elongated, with an average length of 3.8 mm and average width of 1.8 mm; 60% are round in shape, with an average diameter of 1.8 mm; lenticel color is from the greyed purple group N187D.

Leaves:

*Shape.*—Considered acute.

*Texture.*—Leathery.

*Sheen.*—Upper surface is glossy.

*Pubescence.*—Lower surface is considered finely pubescent.

*Blade length.*—98 to 113 mm, average 107 mm.

*Blade width.*—49 to 63 mm, average 56 mm.

*Petiole.*—Medium in length, 33.2 to 46 mm with an average of 40.1 mm. diameter at blade attachment 1.4 to 1.9 mm, with an average of 1.6 mm; finely pubescent, color from the yellow green group 145D.

*Margin.*—Serrate.

*Tip.*—Acuminate.

*Base.*—Rounded.

*Stipules.*—Small and insignificant, in pairs, pointed and averaging 8.5 mm in length and 2.3 mm in width.

*Leaf color.*—Upper surface from the yellow green group 147A; lower surface from the yellow green group 147B.

Flowers: Full bloom date Apr. 28, 2007, in Quincy, Wash.

*Size.*—Individual flowers, medium in size, averaging 43.8 mm in diameter when fully open.

*Petal.*—Average width is 13.4 mm; average length is 18.7 mm.

*Color.*—From the white group N155D with highlights from the red purple group 708.

*Stamen.*—Filament length ranges from 3.4 mm to 8.1 mm, with an average of 5.9 mm; anther length averages 2.5 mm, with color at maturity being from the yellow group 10D.

*Pistil.*—Medium short, with an average length of 10.1 mm; color is from the yellow green group 144C.

*Styles.*—Generally 5 in number, with an occasional 6; fused at base with pubescence present and a color of white from the union down; average length 6.5 mm.

*Stigma.*—Is straight up.

*Sepals.*—Curled down and occasionally inward; average length is 7.8 mm with an average width, of 4.4 mm; color is from the yellow green group 145A with tips occasionally highlighted from the red purple group 71A.

Fruit: Observations and testing from fruit grown in Quincy, Wash.

*Size.*—Considered medium, with an average diameter of 7.47 cm.

*Form.*—Round conical, light ribbing, 5-crowned, and symmetrical.

*Skin texture.*—Smooth with a light bloom.

*Skin appearance.*—Mostly blush with light striping; blush color from the red group 47A and covering 80% to 95% of the surface; stripe color from the red group 53B.

*Stem.*—Considered medium long in length, averaging 3.3 cm in length.

*Stem cavity.*—Average width is 3.2 cm; average depth is 1.8 cm.

*Basin cavity.*—Average width is 2.8 cm; average depth is 1.0 cm.

*Calyx.*—Eye is considered erect with reflexed tips.

*Core.*—Core position is considered distant; core line is marginal.

*Cell.*—Tufted; nearly absent.

*Cell shape.*—Elliptical.

*Tube.*—Funnel shaped.

*Stamen position.*—Median position.

*Axis.*—Axial and open.

*Seed.*—Number: 1 to 2 per cell. Shape: obtuse approaching acute. Color: from the greyed orange group 166A.

*Flesh.*—Juicy, firm, texture is more melting than crisp, flavor is mildly sub-acid and delicate, aroma is slightly aromatic, overall quality is considered very good.

*Average harvest maturity indices.*—Brix at harvest maturity about 14.2 degrees; pressure at harvest maturity averaged 24.0 pounds. starch is 2.8 on 1 to 6 scale where 1 is high starch and 6 is no detectable starch.

*Date of harvest maturity.*—Aug. 13, 2007, in Quincy, Wash.

*Keeping quality.*—Up to 90 days in common storage.

Pollination: Any diploid apple of the same bloom season.

Use: Primarily for fresh eating. Disease and Insect Resistance: is considered to be susceptible to all insects and diseases found in the region of Central Washington.

Variants in botanical details: 'Burnett Gala' exhibits the above-described characteristics as grown in Quincy, Wash. It is expected that differences may occur when grown in areas exhibiting different growing conditions.

I claim:

1. A new and distinct variety of apple tree as herein shown and described.

* * * * *

| | Ultrared | Burnett | Ultrared | | |
|---|---|---|---|---|---|
| sample date* | 8/13/2007 | 8/13/2007 | 8/27/2007 | | |
| Brix | 11.6 | 14.2 | 14.1 | | |
| Presure (lb's) | 24.7 | 24 | 19.5 | | |
| Starch ** | 1.8 | 2.8 | 2.1 | | |
| | * harvest maturity date | | | | |
| | ** scale of 0 - 6 where 6 = high starch, 0 = no starch | | | | |

*Fig. 7.*